United States Patent [19]
Imoto

[11] Patent Number: 5,453,074
[45] Date of Patent: Sep. 26, 1995

[54] ELECTROMAGNETIC THERAPY APPARATUS

[75] Inventor: Tetsuro Imoto, Imari, Japan

[73] Assignee: Yuugenkaisha World Nikken, Saga, Japan

[21] Appl. No.: 170,340

[22] PCT Filed: May 28, 1993

[86] PCT No.: PCT/JP93/00718

§ 371 Date: Jan. 3, 1994

§ 102(e) Date: Jan. 3, 1994

[87] PCT Pub. No.: WO93/24179

PCT Pub. Date: Dec. 9, 1993

[30] Foreign Application Priority Data

Jun. 1, 1992 [JP] Japan ..................... 4-140451

[51] Int. Cl.$^6$ ............................. A61N 1/00
[52] U.S. Cl. ............................. 600/15
[58] Field of Search ............. 600/9–15; 607/100–103

[56] References Cited

U.S. PATENT DOCUMENTS 5,084,003  1/1992  Susic ......................... 600/15

FOREIGN PATENT DOCUMENTS

| 2610589 | 9/1977 | Germany | 600/9 |
| 4018063 | 12/1991 | Germany | 600/9 |
| 2232069 | 9/1990 | Japan . | |
| 42368 | 1/1992 | Japan . | |

*Primary Examiner*—Lee S. Cohen
*Assistant Examiner*—John P. Lacyk
*Attorney, Agent, or Firm*—Jordan and Hamburg

[57] ABSTRACT

An electromagnetic therapy apparatus aimed at heightening the excellent therapeutic effect of an electromagnetic therapy device, making general therapy possible with the conventional electromagnetic therapy device, and being easily used even for patients with reduced physical strength, such as debilitated patients, equipped with frames for the head, upper body and lower body 2, 3, 4 shaped to cover the head, upper body and lower body, respectively, and electromagnetic therapy devices 10 installed in each of the frames 2, 3, 4 to generate an alternating magnetic field towards each part of the body.

3 Claims, 4 Drawing Sheets

ELECTROMAGNETIC THERAPY APPARATUS

BACKGROUND OF THE INVENTION

The present invention relates to an electromagnetic therapy apparatus, and it relates particularly to an electromagnetic therapy apparatus which is suitable for the therapy of the entire human body, particularly the head, lumbar region, legs, etc.

BACKGROUND ART

There have been many hitherto published reports regarding the influence of magnetism on the human body, and various magnetic therapy apparatuses for making use of this magnetism have been proposed.

Of these, the Biobeam (registered trademark), Medical Device Approval No. 59B-1200 available from Nihon Kenko Zoshin Kenkyukai K. K., disclosed in U.S. Pat. No. 4,850,340, is in wide use due to its excellent therapeutic effects.

This electromagnetic therapy device utilizes an alternating magnetic field obtained by running an alternating current through an electromagnet. This creates an alternating line of magnetic force of about 550 gauss to penetrate deep into the part of the body on which it has been mounted, providing an excellent therapeutic effect. The warmth and pleasant slight vibrations produced thereby may enhance this effect.

This electromagnetic therapy device is constructed with five connected folding magnetic pole surfaces so as to fit onto any part of the body, and when used it is wrapped around the site to be treated, such as the shoulders, arms, thighs, legs, etc.

Thus, the above mentioned electromagnetic therapy device according to the prior art is used for so-called local therapy, and is not suited for general therapy.

In addition, a single electromagnetic therapy device unit weighs about 2,500 g, and, when it is fitted onto a local part of or the entire body as described above, it creates pressure pain and discomfort for weakened patients suffering from, particularly, rheumatism and cerebrohematogenic disorders (panplegia or hemiplegia).

Here, the object of the present invention is to raise the effectiveness of the above mentioned electromagnetic therapy device, which has an excellent therapeutic effect, thus making it possible to treat the entire body with electromagnetic therapy devices according to the prior art, while providing an electromagnetic therapy apparatus which can be used even by patients with reduced physical strength, such as debilitated patients.

SUMMARY OF THE INVENTION

The electromagnetic therapy apparatus according to the present invention has achieved the above mentioned object by being equipped with frames for the head, upper body and lower body shaped to cover the head, upper body and lower body, respectively, and having electromagnetic therapy devices installed on each frame to generate an alternating magnetic field towards each part of the body.

The electromagnetic therapy apparatus according to the present invention is constructed so that the head, upper body and lower body are simply slipped into said pre-shaped frames for the head, upper body and lower body, respectively, and are subjected to the action of an alternating line of magnetic force which has a therapeutic effect on the entire body, without pressure being applied to the body.

As a result, electromagnetic therapy becomes possible for the entire body without applying any weight to the body. Also, it is possible to heighten the effect of the electromagnetic therapy since the magnetic therapy becomes possible for the entire body. Furthermore, the patient may use it while lying down, providing the effect of a relaxing therapy, etc.

DETAILED DESCRIPTION OF THE PREFERRED EMBODIMENTS

Figure 1:
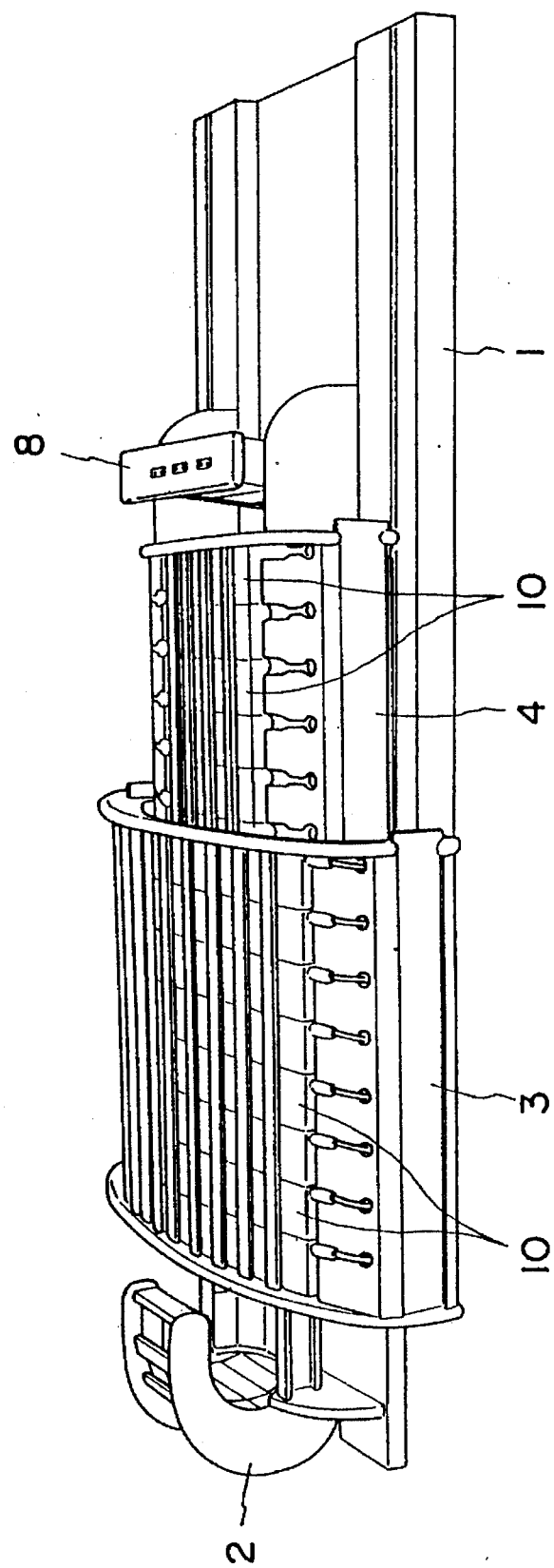
FIG. 1 is a perspective view showing an example of an electromagnetic therapy apparatus according to the present invention when in use.
Figure 2:
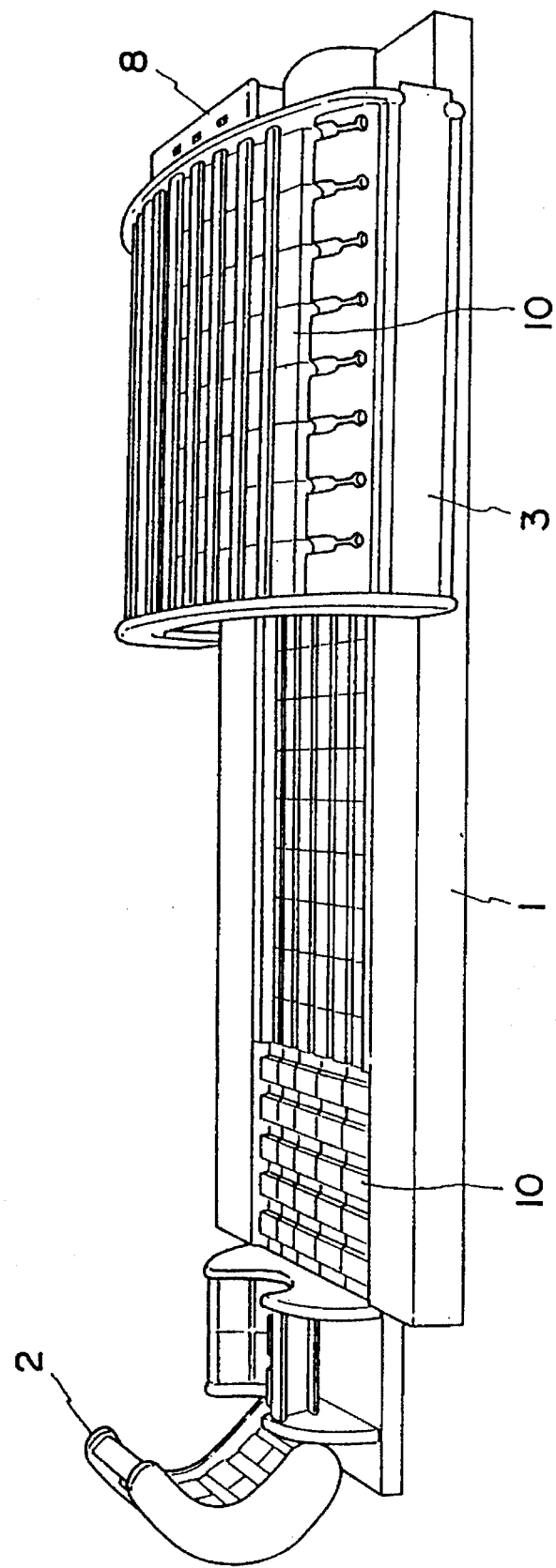
FIG. 2 is a perspective view showing an example of an electromagnetic therapy apparatus according to the present invention when not in use.

Referring to FIGS. 1 and 2, this example of the electromagnetic therapy apparatus consists primarily of a base 1, a head frame 2 provided on one end of the base 1, and an upper body frame 3 and a lower body frame 4 placed over the base 1.

Figure 3:
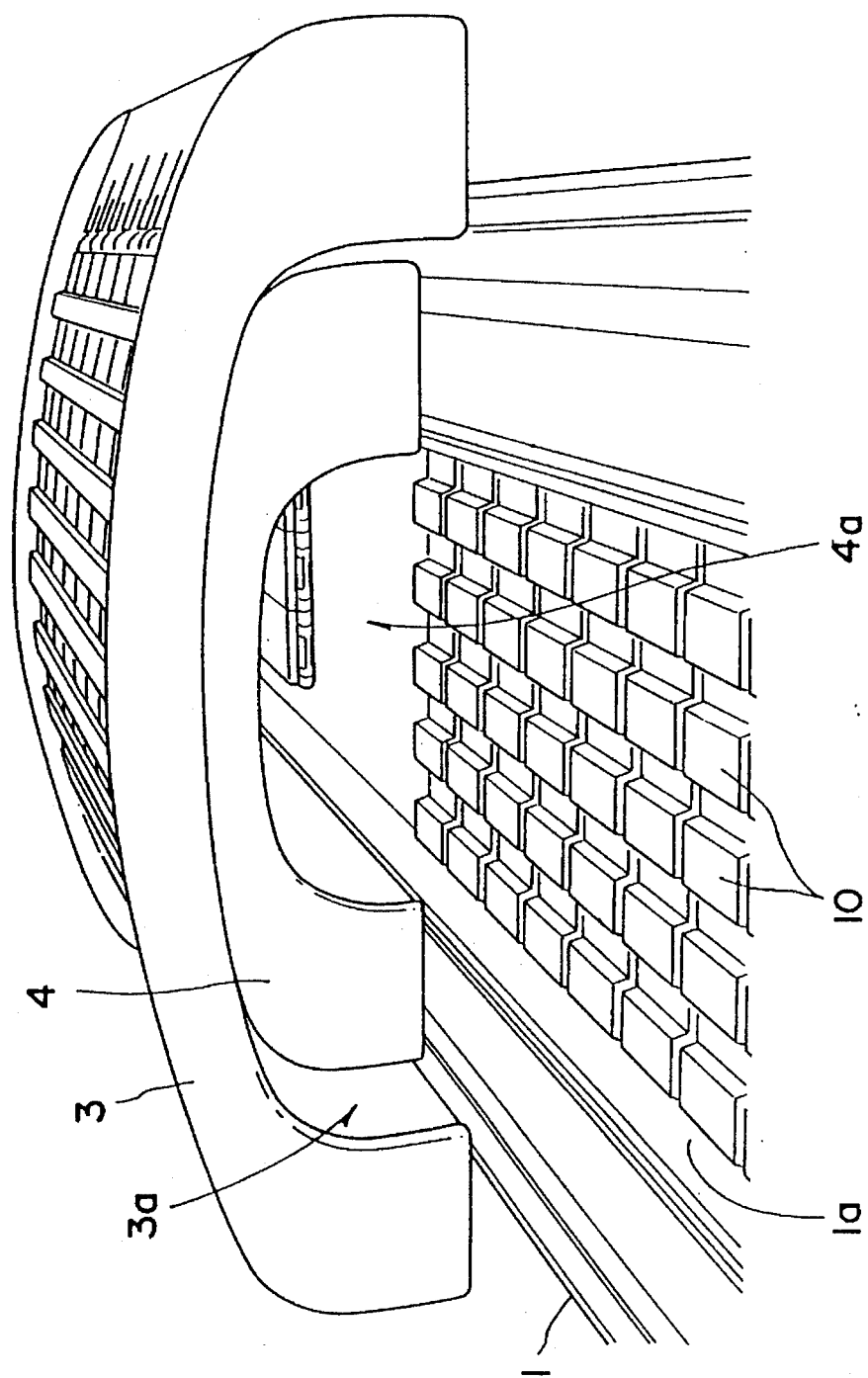
FIG. 3 is a perspective view of the electromagnetic therapy apparatus shown in FIG. 1, as seen from the head frame end.

The base 1 is substantially flat, and may be placed on tatami or carpet, etc. for use. As shown in FIG. 3, a concave section 1a is provided in the center so that electromagnetic therapy devices 10 according to the prior art described above can be inserted into said concave section 1a.

Figure 4:
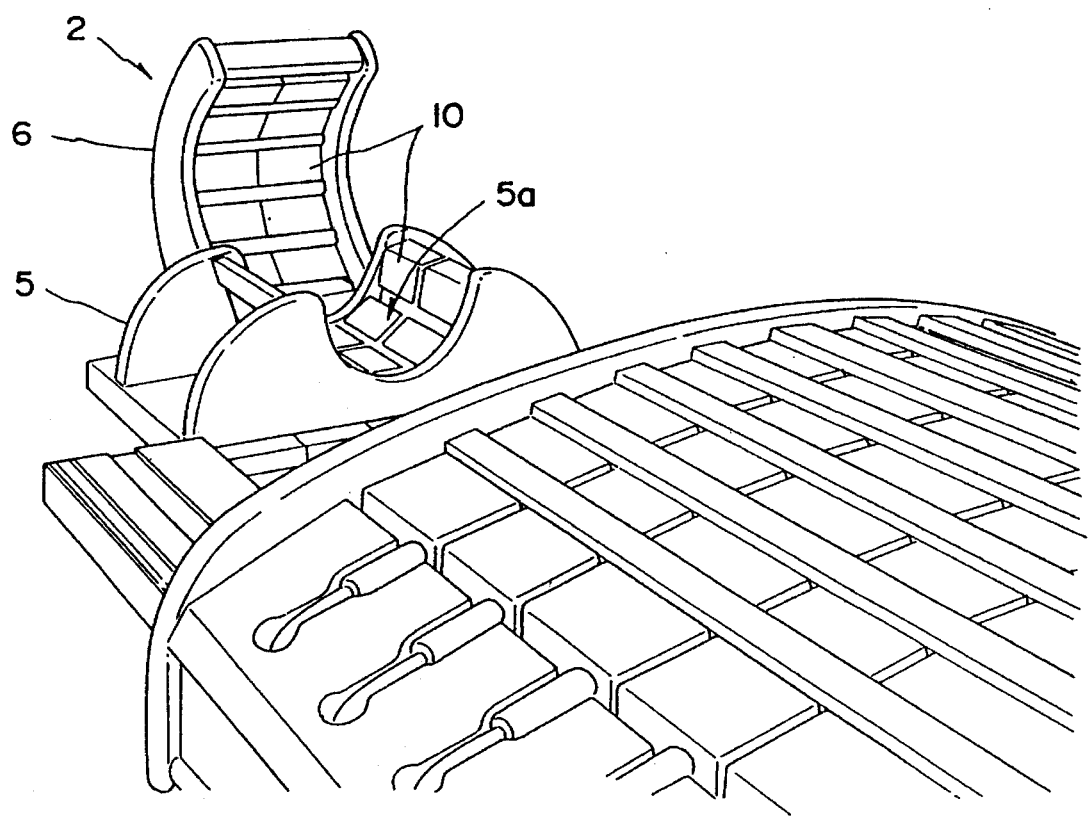
FIG. 4 is a perspective view of the head frame of the electromagnetic therapy apparatus shown in FIG. 1.

The head frame 2, as shown in FIG. 4, is constructed of a base 5 having a concave section 5a for placing the back of the head, and a head cover 6 rotatably connected to the base 5 at the proximal end thereof, the edge of the head cover 6 projecting out over the nose when in use. In addition, electromagnetic therapy devices 10 are installed on all of the surfaces of the concave section 5a of the base 5 and the inside surface of the head cover 6.

The upper body frame 3 and lower body frame 4 provided over the base 1 have, respectively, a semicylindrical hollow section 3a for insertion of the upper body and a semicylindrical hollow section 4a for insertion of the legs, as may best be seen in the angular view in FIG. 3. Both frames 3, 4 are able to slide over the base 1. In addition, the lower body frame 4 may be inserted into the hollow section 3a of the upper body frame 3. Furthermore, electromagnetic therapy devices 10 are installed on all of the upper surfaces of the frames 3, 4.

A foot frame 8 is furnished at the end of the lower body frame 4, and electromagnetic therapy devices 10 are installed therein in a longitudinal direction.

The electromagnetic therapy devices 10 installed in the base 1, head frame 2, upper body frame 3, lower body frame 4 and foot frame 8 are connected to a controller not shown in the drawings, the controller being connected to a household power source. This controller permits independent operation of the electromagnetic therapy devices 10 installed in the base 1, head frame 2, upper body frame 3, lower body frame 4 and foot frame 8. Naturally, all of the devices may be operated simultaneously. In addition, the controller is equipped with a timer, which allows the setting of the desired time of operation of the electromagnetic therapy devices 10 installed in each frame.

An explanation will now be given regarding a method of using an electromagnetic therapy apparatus constructed in the manner described above, with reference to FIGS. 1 and 2.

First, the head frame 2 is opened as shown in FIG. 2, and the upper body frame 3 and lower body frame 4 are slid to the right end as shown in the drawing.

With the apparatus in this state, the patient lies down on the base 1 facing upward. Then, the head frame is put in place as shown in FIG. 1, and, adjusted to the height of the user, the upper body frame 3 and the lower body frame 4 are slid so as to cover the upper body and the lower body from the waist down, respectively, and finally the switches (not shown) of each of the electromagnetic therapy devices 10 are turned on.

As a result, alternating lines of magnetic force are generated towards the body from the plurality of electromagnetic therapy devices 10, over all the surfaces of the head, upper body and lower body, including the soles of the feet, and thus the effect of the magnetic therapy is provided to the entire body. In addition, since the weight of the magnetic generators does not rest on the patient himself, it may be easily used for patients with reduced physical strength, or those who are suffering from rheumatism, hemiplegia, and the like.

Furthermore, the rails at both sides may be replaced for raising and lowering the upper body frame 3 and lower body frame 4 in order to match their heights to the physical frame of the patient.

In the above example, while the upper body and lower body frames 3, 4 may be slid horizontally, they are by no means limited to such a construction, as they may even be double-door hinged-type. Furthermore, the material to be used for their construction may be wood, resin, etc. Also, the upper body and lower body frames 3, 4 may be constructed so as to be slid automatically by electric motor or compressed air.

The electromagnetic therapy apparatus according to the present invention may be favorably used for the electromagnetic therapy of patients with reduced physical strength, such as debilitated patients, who cannot be subjected to general therapy using the electromagnetic therapy device disclosed in U.S. Pat. No. 4,850,340 or to the pressure of weight on the body.

I claim:

1. An apparatus for emitting electromagnetic energy to a body of a person, comprising:

a substantially flat base having a center concave section;

a head frame provided on one end of the base, said head frame including:
 a head base having a concave section for receiving a back of a head of the person,
 a head cover pivotally connected to the head base at a proximal end thereof so that an edge of the head cover projects over a nose of the person during use of said apparatus, and an upper body frame positionable over the base, said upper body frame including a generally semi-cylindrical hollow section for insertion of an upper body of the person therein;

a lower body frame positionable over the base, said lower body frame including a generally semi-cylindrical hollow section for insertion of legs of the person therein;

a foot frame provided at an opposite end of the flat base; and electromagnetic devices for emitting electromagnetic energy, and installed on:
 said center concave section of said substantially flat base,
 surfaces of said concave section of said head base,
 an inner surface of said head cover, surfaces of said upper body frame, surfaces of said lower body frame, and said foot frame in a longitudinal direction thereof.

2. An apparatus according to claim 1, wherein each of said upper body frame and said lower body frame are slidable over said flat base, and said lower body frame is slidable into the hollow section of said upper body frame.

3. An apparatus according to claim 1, wherein each of said upper body frame and said lower body frame are hingedly connected to said flat base.

* * * * *